(12) United States Patent
Dassel et al.

(10) Patent No.: US 6,288,270 B1
(45) Date of Patent: *Sep. 11, 2001

(54) METHODS FOR CONTROLLING THE REACTION RATE OF A HYDROCARBON TO AN ACID BY MAKING PHASE-RELATED ADJUSTMENTS

(75) Inventors: Mark William Dassel, Indianola, WA (US); Eustathios Vassiliou, Newark, DE (US); David Cole DeCoster, Buckley, WA (US); Ader Meherban Rostami, Bainbridge Island, WA (US); Sharon Marie Aldrich, Poulsbo, WA (US)

(73) Assignee: RPC Inc., Atlanta, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/812,847

(22) Filed: Mar. 6, 1997

Related U.S. Application Data (60) Provisional application No. 60/020,798, filed on Jun. 24, 1996.

(51) Int. Cl.⁷ .................................................. C07C 51/16
(52) U.S. Cl. ........................... 562/408; 562/543; 528/272
(58) Field of Search .................................. 562/543, 408; 528/272

(56) References Cited

U.S. PATENT DOCUMENTS

| | | |
|---|---|---|
| 1,121,532 | 12/1914 | Newberry . |
| 2,014,044 | 9/1935 | Haswell ................................... 75/17 |
| 2,223,493 * | 12/1940 | Loder .................................... 562/543 |
| 2,223,494 | 12/1940 | Loder et al. .......................... 260/586 |
| 2,301,240 | 11/1942 | Baumann et al. .................... 183/115 |
| 2,439,513 | 4/1948 | Hamblet et al. ...................... 260/533 |
| 2,557,282 | 6/1951 | Hamblet et al. ...................... 260/533 |
| 2,565,087 | 8/1951 | Porter et al. .......................... 260/631 |
| 2,980,523 | 4/1961 | Dille et al. .............................. 48/215 |
| 3,161,603 | 12/1964 | Leyshon et al. ...................... 252/413 |
| 3,231,608 * | 1/1966 | Kollar .................................... 562/543 |
| 3,234,271 | 2/1966 | Barker et al. ......................... 260/531 |
| 3,290,369 | 12/1966 | Bonfield et al. ...................... 260/537 |
| 3,361,806 | 1/1968 | Lidov et al. .......................... 260/531 |
| 3,515,751 | 6/1970 | Oberster et al. ...................... 260/533 |
| 3,530,185 | 9/1970 | Pugi ...................................... 260/586 |
| 3,613,333 | 10/1971 | Gardenier ................................ 55/89 |
| 3,677,696 | 7/1972 | Bryk et al. ................................. 23/2 |
| 3,839,435 | 10/1974 | Shigeyasu et al. ............... 260/524 R |
| 3,928,005 | 12/1975 | Laslo ...................................... 55/73 |
| 3,932,513 | 1/1976 | Russell ................................. 260/586 |
| 3,946,076 | 3/1976 | Paasen et al. ..................... 260/586 P |
| 3,957,876 | 5/1976 | Rapoport et al. .................... 260/586 |
| 3,987,100 | 10/1976 | Bernette et al. ...................... 260/586 |
| 3,987,808 | 10/1976 | Carbonell et al. ........................ 137/3 |
| 4,025,498 | 5/1977 | Buss et al. .......................... 260/95 A |
| 4,032,569 | 6/1977 | Onopchenko et al. ........... 260/533 C |
| 4,039,304 | 8/1977 | Bechthold et al. ...................... 55/10 |
| 4,055,600 | 10/1977 | Langley et al. ................... 260/586 P |
| 4,065,527 | 12/1977 | Graber ................................ 261/79 A |

(List continued on next page.)

FOREIGN PATENT DOCUMENTS

| | | | |
|---|---|---|---|
| 4426132A1 | 1/1996 | (DE) . | |
| 0439007A2 | 7/1991 | (EP) | .............................. C07C/68/38 |
| 0729084A1 | 8/1996 | (EP) | .............................. G05D/11/13 |
| 0729085A1 | 8/1996 | (EP) | .............................. G05D/11/13 |
| 0751105A2 | 1/1997 | (EP) | .............................. C07B/33/00 |
| 415172 | 8/1934 | (GB) | ................................... 8132/33 |
| 738808 | 10/1955 | (GB) | ......................................... 2/3 |
| 864106 | 3/1961 | (GB) . | |
| 1143213 | 2/1969 | (GB) | ..................................... 51/16 |
| 2014473A | 8/1979 | (GB) | ............................... C07B/3/00 |
| WO 96/03365 | 2/1996 | (WO) . | |
| WO 96/40610 | 12/1996 | (WO) | ..................................... 51/16 |

OTHER PUBLICATIONS

E. Sorribes et al., "Formación de neuvas fases en el proceso de obtención de ácido adípico: causas y efectos que provocan," *Rev. R. Acad. Cienc. Exactas, Fis. Nat. Madrid* (1987), 81 (1), 233–5 (+English language translation).

*Primary Examiner*—Rosalynd Keys
(74) *Attorney, Agent, or Firm*—Seed Intellectual Property Law Group PLLC (57) ABSTRACT

Methods for controlling the reaction rate of a hydrocarbon to an acid by making phase-related adjustments are disclosed. In order to improve reaction rate of the oxidation, a single phase at the operating temperature is attained and maintained by adjusting one or more of gaseous oxidant flow rate, pressure in the reaction zone, temperature in the reaction zone, feed rate of hydrocarbon, feed rate of solvent, feed rate of water if water is being fed, feed rate of the catalyst. The preferred hydrocarbon is cyclohexane, the preferred acid is adipic acid, the preferred solvent is acetic acid, and the preferred catalyst is cobalt acetate. Other hydrocarbons include, but are not limited to, methylated benzene, methylated structures involving two benzene rings, and methylated naphthalene.

71 Claims, 3 Drawing Sheets

U.S. PATENT DOCUMENTS

| | | | |
|---|---|---|---|
| 4,158,739 | 6/1979 | Schulz et al. | 562/543 |
| 4,160,108 * | 7/1979 | Shigeyasu et al. | 562/416 |
| 4,263,453 | 4/1981 | Schulz et al. | 562/543 |
| 4,308,037 | 12/1981 | Meissner et al. | 55/10 |
| 4,332,590 | 6/1982 | Smith | 23/230 A |
| 4,361,965 | 12/1982 | Goumondy et al. | 34/57 R |
| 4,370,304 | 1/1983 | Hendriks et al. | 422/224 |
| 4,394,139 | 7/1983 | Board | 55/20 |
| 4,419,184 | 12/1983 | Backlund | 162/49 |
| 4,423,018 | 12/1983 | Lester, Jr. et al. | 423/243 |
| 4,603,220 * | 7/1986 | Feld | 562/416 |
| 5,061,453 | 10/1991 | Krippl et al. | 422/106 |
| 5,104,492 | 4/1992 | King et al. | 203/15 |
| 5,123,936 | 6/1992 | Stone et al. | 55/8 |
| 5,170,727 | 12/1992 | Nielsen | 110/346 |
| 5,221,800 * | 6/1993 | Park et al. | 562/543 |
| 5,244,603 | 9/1993 | Davis | 261/87 |
| 5,270,019 | 12/1993 | Melton et al. | 422/234 |
| 5,271,904 | 12/1993 | Esposito et al. | 422/105 |
| 5,286,458 | 2/1994 | Yang et al. | 422/168 |
| 5,294,378 | 3/1994 | Succi et al. | 261/130 |
| 5,312,567 | 5/1994 | Kozma et al. | 261/87 |
| 5,321,157 | 6/1994 | Kollar | 562/543 |
| 5,374,767 | 12/1994 | Drinkard et al. | 560/193 |
| 5,396,850 | 3/1995 | Conochie et al. | 110/346 |
| 5,399,750 | 3/1995 | Brun et al. | 562/553 |
| 5,463,119 | 10/1995 | Kollar | 562/543 |
| 5,502,245 | 3/1996 | Dassel et al. | 562/413 |
| 5,516,423 | 5/1996 | Conoby et al. | 210/85 |
| 5,558,842 | 9/1996 | Vassiliou et al. | 422/108 |
| 5,580,531 | 12/1996 | Vassiliou et al. | 422/108 |
| 5,654,475 * | 8/1997 | Vassiliou et al. | 562/413 |
| 5,756,837 | 5/1998 | Costantini et al. | 562/543 |

* cited by examiner

METHODS FOR CONTROLLING THE REACTION RATE OF A HYDROCARBON TO AN ACID BY MAKING PHASE-RELATED ADJUSTMENTS

CROSS-REFERENCE TO RELATED APPLICATION

The present application claims the benefit of U.S. Provisional Application No. 60/020,798, filed Jun. 24, 1996, which application is incorporated herein by reference in its entirety.

FIELD OF THE INVENTION

This invention relates to methods of making intermediate oxidation products, such as acids, for example, by oxidizing a hydrocarbon with a gas containing an oxidant, preferably oxygen.

BACKGROUND OF THE INVENTION

There is a plethora of references (both patents and literature articles) dealing with the formation of diacids, one of the most important being adipic acid. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process", the "Boric Acid Process", and the "Direct Synthesis Process", which involves direct oxidation of cyclohexane to adipic acid with oxygen in the presence of solvents, catalysts, and promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar Phase" and the "Non-Polar" phase. However, no attention has been paid so far to the importance of the two phases, except for separating the adipic acid from the "Polar Phase" and recycling these phases to the reactor partially or totally with or without further treatment.

It is also important to note that most, if not all, studies on the Direct Oxidation have been conducted in a batch mode, literally or for all practical purposes.

There is a plethora of references dealing with oxidation of organic compounds to produce acids, such as, for example, adipic acid and/or intermediate products, such as for example cyclohexanone, cyclohexanol, cyclohexylhydroperoxide, etc.

The following references, among the plethora of others, may be considered as representative of oxidation processes relative to the preparation of diacids and intermediate products.

U.S. Pat. No. 5,463,119 (Kollar) discloses a process for the oxidative preparation of $C_5$–$C_8$ aliphatic dibasic acids by (1) reacting,
  (a) at least one saturated cycloaliphatic hydrocarbon having from 5 to 8 ring carbon atoms in the liquid phase and
  (b) an excess of oxygen gas or an oxygen-containing gas in the presence of
  (c) a solvent comprising an organic acid containing only primary and/or secondary hydrogen atoms and
  (d) at least about 0.002 mole per 1000 grams of reaction mixture of a polyvalent heavy metal catalyst;
(2) removing the aliphatic dibasic acid; and
(3) recycling intermediates, post oxidation components, and derivatives thereof remaining after removal of the aliphatic dibasic acid into the oxidation reaction.

U.S. Pat. No. 5,374,767 (Drinkard et al) discloses formation of cyclohexyladipates in a staged reactor, e.g. a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of $C_5$–$C_8$ aliphatic dibasic acids through oxidation of corresponding saturated cycloaliphatic hydrocarbons by (1) reacting, at a cycloaliphatic hydrocarbon conversion level of between about 7% and about 30%,
  (a) at least one saturated cycloaliphatic hydrocarbon having from 5 to 8 ring carbon atoms in the liquid phase and
  (b) an excess of oxygen gas or an oxygen containing gas mixture
in the presence of
  (c) less than 1.5 moles of a solvent per mole of cycloaliphatic hydrocarbon (a), wherein said solvent comprises an organic acid containing only primary and/or secondary hydrogen atoms and
  (d) at least about 0.002 mole per 1000 grams of reaction mixture of a polyvalent heavy metal catalyst; and
(2) isolating the C5–C8 aliphatic dibasic acid.

U.S. Pat. No. 5,221,800 (Park et al) discloses a process for the manufacture of adipic acid. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 1500° C. at an oxygen partial pressure of about 50 to 420 pounds per square inch absolute.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Oberster et al) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al) discloses production of adipic acid and related aliphatic dibasic acids; more particularly to the production of adipic acid by the direct oxidation of cyclohexane.

U.S. Pat. No. 2,439,513 (Hamblet et al) discloses; the production of adipic acid and related aliphatic dibasic acids and more particularly to the production of adipic acid by the oxidation of cyclohexane.

U.S. Pat. No. 2,223,494 (Loder et al) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al) discloses the production of aliphatic dibasic acids and more particularly to the production of aliphatic dibasic acids by oxidation of cyclic saturated hydrocarbons with an oxygen-containing gas.

None of the above references, or any other references known to the inventors disclose, suggest or imply, singly or in combination, oxidation reactions to intermediate oxidation products under phase-controlled conditions subject to the intricate and critical controls and requirements of the instant invention as described and claimed.

Our U.S. Pat. Nos. 5,580,531, 5,558,842, 5,502,245, and our co-pending applications 08/477,195 (filed Jun. 07,1995), 08/587,967 (filed Jan. 17,1996), and 08/620,974 (filed Mar. 25,1996), all of which are incorporated herein by reference, describe methods and apparatuses relative to controlling reactions in atomized liquids.

SUMMARY OF THE INVENTION

As aforementioned, this invention relates to methods of making intermediate oxidation products, such as acids, for example, by oxidizing a hydrocarbon with a gas containing an oxidant, preferably oxygen. More particularly, it relates to a method of controlling in a reaction zone the oxidation of a hydrocarbon to form an acid in the presence of a catalyst, a solvent, optionally a promoter, and oxidation products including water, the hydrocarbon, the catalyst, the solvent, and at least part of the oxidation products including water forming at least partially a liquid mixture, the method comprising the steps of:

(a) bringing in contact the liquid mixture with a gaseous oxidant in a reaction zone at a first temperature, the first temperature being adequately high for the oxidation to proceed; and (b) making phase-related adjustments to the liquid mixture, the phase-related adjustments being at least partially based on phase formation relationships when said liquid mixture is at a second temperature.

Preferably, the first and the second temperatures are substantially the same. The second temperature, however, may be any other temperature or substantially ambient temperature in the range of about 20° to 25° C.

Also preferably, the phase related adjustments to the liquid mixture are directed toward formation and maintenance of a single liquid phase at the first temperature.

The phase related adjustments to the liquid mixture may be conducted by controlling in the reaction zone a variable selected from a group consisting of temperature in the reaction zone, pressure in the reaction zone, rate of gaseous oxidant flow, water feed rate, catalyst feed rate, hydrocarbon feed rate, solvent feed rate, and a combination thereof.

The hydrocarbon may be a cyclic aliphatic hydrocarbon, preferably having 5 to 12 carbon atoms, and more preferably comprising cyclohexane.

It is preferable that the gaseous oxidant comprises oxygen, the solvent comprises acetic acid, the catalyst comprises cobalt ions and the promoter comprises acetaldehyde or cyclohexanone. It is also preferable that the oxidation products comprise adipic acid and water.

The hydrocarbon may be a methylated aromatic: hydrocarbon, such as mono- or poly- methyl benzene, mono- or poly- methyl naphthalene, and the like, for example. Preferably, the methylated aromatic hydrocarbon comprises toluene and the acid comprises benzoic acid. More preferably, the methylated aromatic hydrocarbon is selected from a group consisting of o-xylene, m-xylene, p-xylene, and a mixture thereof, and the acid is selected from a group consisting of phthalic acid, isophthalic acid, terephthalic acid, and a mixture thereof.

The methods of this invention may further comprise a step of atomizing the liquid mixture, or a step of stirring the liquid mixture, or both.

The methods of the instant invention may also comprise a step of correlating phase diagram data with variables selected from a group consisting of temperature in the reaction zone, pressure in the reaction zone, rate of gaseous oxidant flow, water feed rate, catalyst feed rate, hydrocarbon feed rate, solvent feed rate, and a combination thereof, in order to control the oxidation of the hydrocarbon by preferably controlling in the reaction zone a variable selected from a group consisting of temperature in the reaction zone, pressure in the reaction zone, rate of gaseous oxidant flow, water feed rate, catalyst feed rate, hydrocarbon feed rate, solvent feed rate, and a combination thereof.

Further, the instant invention pertains a method, wherein the acid comprises a compound selected from a group consisting of adipic acid, phthalic acid, isophthalic acid, and terephthalic acid, and the method further comprises a step of reacting acid with a third reactant selected from a group consisting of a polyol, a polyamine, and a polyamide in a manner to form a polymer of a polyester, or a polyamide, or a (polyimide and/or polyamideimide), respectively.

The method may further comprise a step of spinning the polymer into fibers.

The present invention also pertains to a device for oxidizing a hydrocarbon, the hydrocarbon being at least partially in a liquid state, with a gaseous oxidant to form an acid, the device comprising:

a reaction chamber;

a temperature monitor connected to the reaction chamber for measuring temperature inside said reaction chamber;

phase detection means for detecting phase-related characteristics of ingredients within the reaction chamber; and phase control means for making phase-related adjustments and controlling the phase characteristics of said ingredients within the reaction chamber.

The phase control means may further comprise temperature control means for controlling the first temperature. They may also comprise correlation means for correlating phase diagram data with ingredients in the reaction chamber, and adjusting feeding rates of said ingredients to the reaction chamber toward formation of a single liquid phase. The phase detection means of the device provide information to the phase control means for adjusting feeding rates of ingredients fed to the reaction chamber toward formation of a single liquid phase.

The device may further comprise atomizing means for atomizing the hydrocarbon, and/or stirring means for stirring the hydrocarbon.

The devices of this invention may also comprise variable control means for controlling in the reaction zone a variable selected from a group consisting pressure in the reaction zone, rate of gaseous oxidant flow, water feed rate, catalyst feed rate, hydrocarbon feed rate, solvent feed rate, and a combination thereof.

BRIEF DESCRIPTION OF THE DRAWING

The reader's understanding of this invention will be enhanced by reference to the following detailed description taken in combination with the drawing figure, wherein.

DETAILED DESCRIPTION OF THE INVENTION

As mentioned earlier, this invention relates to methods of making intermediate oxidation products, such as acids, for example, by oxidizing a hydrocarbon with a gas containing an oxidant, preferably oxygen.

A tubular rocking mini-reactor containing steel balls was used for a series of experiments. The steel balls were added to provide highly enhanced surface factor by means of distributing a thin film on the surface of the steel balls. Surface factor is defined in this case as the ratio of the surface of the liquid/gas interface per unit volume of the liquid. The mini-reactor comprised a tubular stainless steel body having an inside diameter of $^{23}/_{32}$", an outside diameter of 2¼", an outside length of about 11½", and an inside length of about 9½". The total capacity of the mini-reactor was 75 cc. Approximately 890 stainless steel balls having a diameter of ⅛" were used in the mini-reactor as agitation and mixing means, along with a rocking action of ±33 degrees from horizontal at a frequency of 10 cycles per minute, unless otherwise stated. The mini-reactor had a screw cap top, a number of thermocouples inside and outside for measuring and controlling the temperature. It was surrounded by heating tape, and insulated by glass fiber. It had ports for feeding gases and liquids. It was also provided with a pressure transducer. Both temperature and pressure were recorded and controlled through a computer using supervisory control software.

In operation of the mini-rector, the following procedure was followed, unless otherwise stated. The system was initially purged with nitrogen, the feed was added, while purging with nitrogen, through the top of the mini-reactor which was in an uncapped position, the mini-reactor was capped and purged again with nitrogen to a pressure of about 50 psig, the temperature was raised to a desired degree (usually 100–105° C.), the pressure was brought to about 100 psig with nitrogen, and the oxygen was introduced to a pressure of an additional 100 psig, thus bringing the total pressure to about 200 psig. The pressure (P) and the rate of pressure drop (dP/dt), among other variables were then recorded. Unless no substantial reaction takes place, the dP/dt goes from substantially zero rate to a maximum, and then it drops off again to substantially zero rate. In the different plots or Tables, when the terms "reaction rate" and "reactivity" are used, they correspond to the maximum dP/dt in each particular case, unless otherwise stated. An initial sharp peak preceding the maximum is disregarded, as it believed to correspond to a fast oxidation of the promoter or initiator, such as acetaldehyde for example. In the case that cyclohexanone is used as promoter or initiator, such a preceding peak is not as sharp or pronounced. Although the terms "promoter" and "initiator" are many times used in the literature and in this work interchangeably, the more strict meaning of the term "initiator" should be used for a substance which decreases the reaction initiation period, such as acetaldehyde or cyclohexanone, or methylethylketone, for example, and the term "promoter" should be used for a substance that promotes the reaction, such as bromide ions in the case of producing terephthalic acid from p-xylene, for example.

The inventors also used a high pressure, agitated, glass tube to determine phase relationships under conditions of actual reaction temperature, pressure, and composition.

Analysis of the products of reaction was conducted by HPLC and GC, both being well known to the art techniques.

After a reaction has taken place in the Direct Synthesis of cyclohexane to adipic acid, a mixture of two liquid phases is present at ambient temperature, along with a solid phase mainly consisting of adipic acid. The two liquid phases have been called the "Polar Phase" and the "Non-Polar" phase. However, no attention has been paid so far to the importance of the two phases, except for separating the adipic acid from the "Polar Phase" and recycling these phases to the reactor partially or totally with or without further treatment.

The inventors of the instant invention, using the above apparatus, unexpectedly discovered that both the composition and a number of relationships between the "Polar" and the "Non-Polar" phases are of utmost importance for the reactions taking place during the Direct Synthesis. They also found out that not only the relationship of the phases at reaction temperature are important, but also even the relationship of the phases at room temperature may be utilized to control the reaction at reaction temperatures, which is totally unexpected, since the phase relationship may change drastically with temperature.

According to the present invention, "Polar Phase" is a liquid phase which contains predominantly polar components, while "Non-Polar Phase" is a liquid phase which contains predominantly non-polar components. In addition, when two liquid phases are present, the one which is more polar than the other is the "Polar Phase" while the one which is less polar is the "Non-Polar Phase". Under certain controlled circumstances, as explained in more detail below, the two phases may merge into one phase, which is called "Single Phase", according to this invention. The "Single Phase" may be a "Single Polar Phase" if it contains predominantly polar components, or a "Single Non Polar-Phase" if it contains predominantly non-polar components. Further, as the temperature increases, one of the two phases may increase and the other decrease. If the "Polar Phase" decreases in a manner to finally be absorbed by the "N,on-Polar Phase", then the "Single Phase" formed is a "Single Non-Polar Phase". Similarly, if the "Non-Polar Phase" decreases in a manner to finally be absorbed by the "Polar Phase", then the "Single Phase" formed is a "Single Polar Phase". Regardless of the type of the phase, "RT" phase is a phase as it exists at ambient or room temperature; "75° C." phase is a phase as it exists at 75° C.; "100° C." phase is a phase as it exists at 100° C., and so on and so forth. Ambient or Room Temperature is about 20° C. When mentioning phases in this discussion, implied reference is made to liquid phases, unless solid phases are specifically cited and stated as such.

For purposes of clarity and brevity, the most preferred constituents may be used to exemplify the methods of the present invention, instead of more generic terms. For example "acetic acid" may be used instead of "solvent", but it should be understood that any other suitable solvent(s) may be used in said methods. Examples of less preferred solvents are butyric acid, propionic acid, etc. In a similar manner, "acetaldehyde" may be used instead of the more generic name "promoter", and "cobalt acetatetetrahydrate", or "cobalt acetate" (both meaning "cobaltous acetate tetrahydrate" unless otherwise specified) may often be used instead of the more generic term "catalyst".

In addition to the formation of adipic acid, the methods of the present invention may also be applied to other diacids from the corresponding cyclic aliphatic hydrocarbons. Examples are formation of glutaric acid from cyclopentane, formation of pimelic acid from cycloheptane, and the like. Further the teachings of this invention may be used for the formation of benzoic acid from toluene, formation of phthalic acid from o-xylene, formation of isophthalic acid from m-xylene, formation of terephthalic acid from p-xylene, and the like.

Since quantity-wise, the major polar component in the reaction mixture is acetic acid having a specific gravity slightly higher than 1 g/cc, and the major non-polar component is cyclohexane having a specific gravity slightly lower than 0.8 g/cc, the polar phase is heavier than the non-polar phase, and if both are present, the non-polar phase tends to move toward the top, while the polar phase tends to move toward the bottom. Thus, in a test tube if a sample has a polar phase and a non-polar phase, the polar phase will reside at the bottom of the tube, and the non-polar phase will reside at the top of the tube.

It was observed by the inventors that addition of very small amounts of water, as well as changes in the amount of cobalt acetate, have a substantial effect on the relationship of the two phases. It is speculated that this occurs because water and cobalt acetate are very polar compounds For example, the composition of Table 1 was found to be in the form of two phases at room temperature. The bottom phase, which is the RT polar phase constituted only about 3% (by volume) of the total, while the RT non-polar phase constituted about 97% (by volume) of the total. At this point it is very important to note that substantially the total amount of the catalyst, as determined calorimetrically, resided in the bottom polar phase. For example, in this instance, the top phase was colorless and clear, while the bottom phase had a dense magenta coloration.

As shown in Tables 2 and 3, after adding about only 0.4% (by weight) water to the composition represented in Table 1, the volume of the RT polar phase grew to about 17% (by volume). As more and more water was added, the RT polar phase increased further, and at about 6% (by weight) water, the RT polar phase constituted about 30% (by volume) of the total. The initial addition of water had considerably higher effect in the increase of RT polar phase than the addition of further amounts of water. However, at low concentrations of cyclohexane and higher concentrations of acetic acid, the water has a considerably lower effect on the ratio of the two phases. During the reaction of cyclohexane with oxygen, a considerable amount of water is produced, and therefore, the presence of water is a fact, and not a matter of choice.

By adding a small amount (about 0.4 to about 1% by weight) of water an appreciable amount of RT polar phase was formed (about 20% by volume). Then, by separating the two phases, and re-mixing them in different proportions to form the totality of a reaction feed mixture, it was found unexpectedly that, in the case of the mini-reactor, the reactivity of the mixture was proportional to the amount of the RT polar phase present, to a certain point and then it dropped. This drop in the batch type mini-reactor may be due to cyclohexane starvation.

TABLE 1

Composition of Stock Solution

| INGREDIENTS | GRAMS | WT % | MOLE % |
|---|---|---|---|
| Cobalt Acetate Tetrahydrate | 0.342 | 0.71 | 0.21 |
| Acetic Acid | 14.679 | 30.58 | 38.09 |
| Acetaldehyde | 0.339 | 0.71 | 1.20 |
| Cyclohexane | 32.635 | 68.00 | 60.49 |
| Total | 47.995 | | |

TABLE 2

Feed solutions containing different amounts of water

| Graduated Cylinder # | | i | ii | iii | iv | v | vi |
|---|---|---|---|---|---|---|---|
| Wt of Empty Cylinder | gm | 52.337 | 34.590 | 34.260 | 35.604 | 39.031 | 34.937 |
| Wt of Cylinder + Stock Solution | gm | 57.394 | 39.743 | 39.444 | 40.967 | 44.490 | 40.130 |
| Wt of the feed solution | gm | 5.057 | 5.153 | 5.184 | 5.363 | 5.459 | 5.193 |
| Wt of Cylinder + Feed Soln. + Water | gm | 57.394 | 39.764 | 39.493 | 41.072 | 44.680 | 40.481 |
| Wt of Water added | gm | 0.000 | 0.021 | 0.049 | 0.105 | 0.190 | 0.351 |
| Wt % of Water added | | 0.00 | 0.41 | 0.94 | 1.92 | 3.36 | 6.33 |

TABLE 3

Volume of RT polar (bottom) Phase as compared to RT Non-Polar (top) Phase

| Graduated Cylinder # | | i | ii | iii | iv | v | vi |
|---|---|---|---|---|---|---|---|
| Volume (ml) before adding water | Top Phase | 6.3 | 6.2 | 6.2 | 6.4 | 6.3 | 6.4 |
| | Bottom Phase | 0.2 | 0.2 | 0.2 | 0.3 | 0.3 | 0.3 |
| Volume (ml) after adding water | Top Phase | 6.3 | 5.3 | 5.1 | 5.3 | 5.0 | 4.8 |
| | Bottom Phase | 0.2 | 1.1 | 1.3 | 1.4 | 1.8 | 2.0 |
| Volume % of the bottom Phase | Before Water addition | 3.1 | 3.1 | 3.1 | 4.5 | 4.6 | 4.5 |
| | After Water addition | 3.1 | 17.1 | 20.31 | 20.9 | 26.5 | 29.4 |

It was also observed that at a level of about 20% RT polar phase, specifically in case iii of Table 3, as the temperature increased, the polar phase progressively shrunk to a very small volume, and finally it disappeared into the non-polar phase at a temperature of about 100° C. The consequence of this was that as the polar phase (which as mentioned before contains most if not substantially all the catalyst) shrunk between 80° and 100° C., at some point it became over-saturated with catalyst, which resulted in catalyst precipitation. This is highly undesirable not only because of the highly decreased availability of catalyst, but also because precipitated matter in a reactor causes loss of reactor and plant utility, and high maintenance cost due to plugging of lines, etc. At about 100° C., most of the precipitated catalyst re-dissolved in the single non-polar phase, while some remained still in the precipitated form. Thus, in this particular case, although a reaction of cyclohexane with oxygen may proceed at temperatures lower than 100° C., the reaction rate and reactivity would be considerably reduced, since the dissolved catalyst level has been reduced. Another consequence of this is that unless one uses a temperature of 100° C., or higher, it is very difficult to bring in contact the bulk of the material, which is the non-polar phase, containing substantially all the cyclohexane available, with the catalyst, all of which substantially resides in the very small amount of the polar phase, and with the gaseous phase of oxygen. Extremely severe stirring or other method of efficient mixing or dispersing, possibly beyond best current practiced technology, would have to be used for increasing the surface factor, defined as the ratio of the surface of the interface of the two liquid phases and the sum of the volumes of the two phases. Water concentration in the reactor, due to water formation, greater than the one represented by cases ii and iii in Table 3, will significantly worsen the aforementioned deleterious effects. Higher temperatures may not always be a practical remedy for these problems, because in order to improve chemical yield it may be advantageous to run the reaction at lower temperatures.

At different relatively low proportions of RT polar phase to RT non-polar phase (about less that 30% or 40% polar phase, in this particular case), there is a phase-critical temperature under which the polar phase, containing most if not substantially all the catalyst, shrinks to very low levels, and therefore the reaction rate and reactivity suffer considerably. It is therefore important to run the reaction at or above that temperature. It is more preferable to run the reaction in a range of temperatures from the phase-critical temperature to about 5° C. above said phase-critical temperature. For different compositions, the phase-critical temperature will vary, but it is very easy to be determined by using a high-pressure transparent glass vial in which the sample is introduced, and the temperature is raised with simultaneous observation of the phase changes.

It should be stressed that as the amount of water present in the composition increases, the shrinkage upon heating of the polar phase decreases, and finally the two phases do not become a single phase, even at elevated temperatures, even at temperatures higher than the desirable reaction temperatures. Thus, in order to attain a single phase, it is preferable that water is controlled by removal, or the amount of solvent increased. As the amount of acetic acid increases in a composition (including both polar and non-polar phases), the composition can withstand the presence of more water for creating a phase-critical temperature within the range of desirable reaction temperatures.

It was also observed that at about 65% RT polar phase, as the temperature increased, the non-polar phase shrunk, and at a temperature of 97° C., it was completely absorbed by the polar phase to form a single polar phase, as defined earlier. Further, it was observed that at higher amounts of water present (about 7% by weight of the total composition), the composition remained in two phases even at 120° C. Thus, it is preferable that the reaction is run in a manner that the amount of water remains adequately low (or removed), so that the formation of two phases at the operating temperature is avoided.

As mentioned above, it was also observed that the larger the amount of the RT polar phase, the faster the reaction up to a certain point. A similar relationship between the maximum pressure drop rate (representing the reaction rate) and the absolute amount of catalyst in the mini-reactor was also observed.

It was also entirely unexpected to find out that the mole % selectivity to adipic acid did not change with wt % RT polar phase present or with the amount of catalyst present. It remained substantially constant. The mole % selectivity to adipic acid is defined as the moles of adipic acid formed in the reaction, multiplied by 100, and divided by the sum of moles formed of adipic, glutaric and succinic acids.

It was also found that the selectivity to adipic acid was independent of the amount of acetaldehyde present or the molar ratio of acetaldehyde to cobalt acetate.

Regarding the RT and other temperature polar and non-polar phases, it should be pointed out that their compositions may vary considerably depending on the amount and nature of catalyst, water, solvent, hydrocarbon, initiator, etc. Thus different conclusions stated hereinbelow are relative to polar and non-polar phases made as described in each particular case. However, a person of ordinary skill in the art, based on the teaching of this invention, may find desired relations of other polar and non polar phases in other occasions with only a minimal effort.

The implications of these finding have an enormous impact in a large number of aspects regarding the direct synthesis of adipic acid by oxidation of cyclohexane with oxygen. These findings indicate the following important process steps, among others, which may be performed to drastically improve and control the oxidation process. These steps may be performed individually or in any combination, depending on the circumstances, including but not limited to reactor design, reactor-peripherals' design, preexisting or new-reactor, parameter limitations, etc.

(1) Since the reactivity shows a maximum at a range of about 65% RT polar phase (as made in composition iii of Table 2) and higher, especially without sacrificing selectivity, the reaction should be driven toward that range of RT polar phase (nevertheless, increase of total catalyst level with increase in RT polar phase should be kept in mind);

(2) Since the reactivity (the amount of reaction taking place in a given reaction volume) shows a similar behavior regarding catalyst level, especially without sacrificing selectivity, the reaction should be driven toward that range of catalyst level, preferably under the precipitation point at which the catalyst starts precipitating;

(3) Since cyclohexane is the main contributor to the formation of the non-polar phase, the reaction should preferably be driven toward the minimum amount of cyclohexane in such a manner that there is always an adequate amount of cyclohexane in the liquid and vapor forms in order to avoid starvation of the reaction because of lack of cyclohexane; in all instances its preferably to be controlled below that amount which causes a second phase to form at reaction conditions; minimization of cyclohexane in the reactor has a very important additional beneficial effect, which is related to safety; in case of accidental ignition in the reactor, there will be considerably less fuel (cyclohexane) to promote an explosion;

(4) Since acetic acid is a main contributor to the formation of the polar phase, the reaction should be driven toward the maximum amount of acetic acid in such a manner that excessive dilution is avoided or prevented; this step should preferably be coordinated with step (3) so that the amount of acetic acid does not cause lowering of the amount of cyclohexane to cause in turn starvation of the reaction because of lack of cyclohexane; preferably, the amount of acetic acid used should be such as to produce a ratio of RT polar phase to RT non-polar phase in the range of over about 65% RT polar phase combined with an adequate amount of cyclohexane to avoid cyclohexane starvation of the reaction;

(5) In order to operate with a single-phase system, which is highly preferable for multiple reasons, the reaction should be maintained at a temperature equal to or higher than the phase-critical temperature (as defined earlier) within limits to ensure that selectivity and yield do not suffer unacceptably;

(6) Since water is a strong contributor to the formation of two phases from a single phase, which is undesirable, but since it is believed to help the hydrolysis of undesirable ester by-products formed during the reaction, and because it is also believed to increase yield and selectivity of adipic acid, its content in the reaction mixture should be driven toward the maximum amount of water which does not cause the formation of a two-phase system from the single phase at least at the reaction temperature.

(7) In order to avoid or prevent precipitation of catalyst at room or lower temperatures at which the adipic acid is crystallized, the amount of catalyst in the mixture should be driven toward a region below the precipitation point of the catalyst in the reacted and cooled mixture;

(8) If it is necessary for any reason to operate with two phases, the mixture should be driven toward a ratio of phases 1:1 for increasing the interfacial surface area between the two phases.

Figure 1:
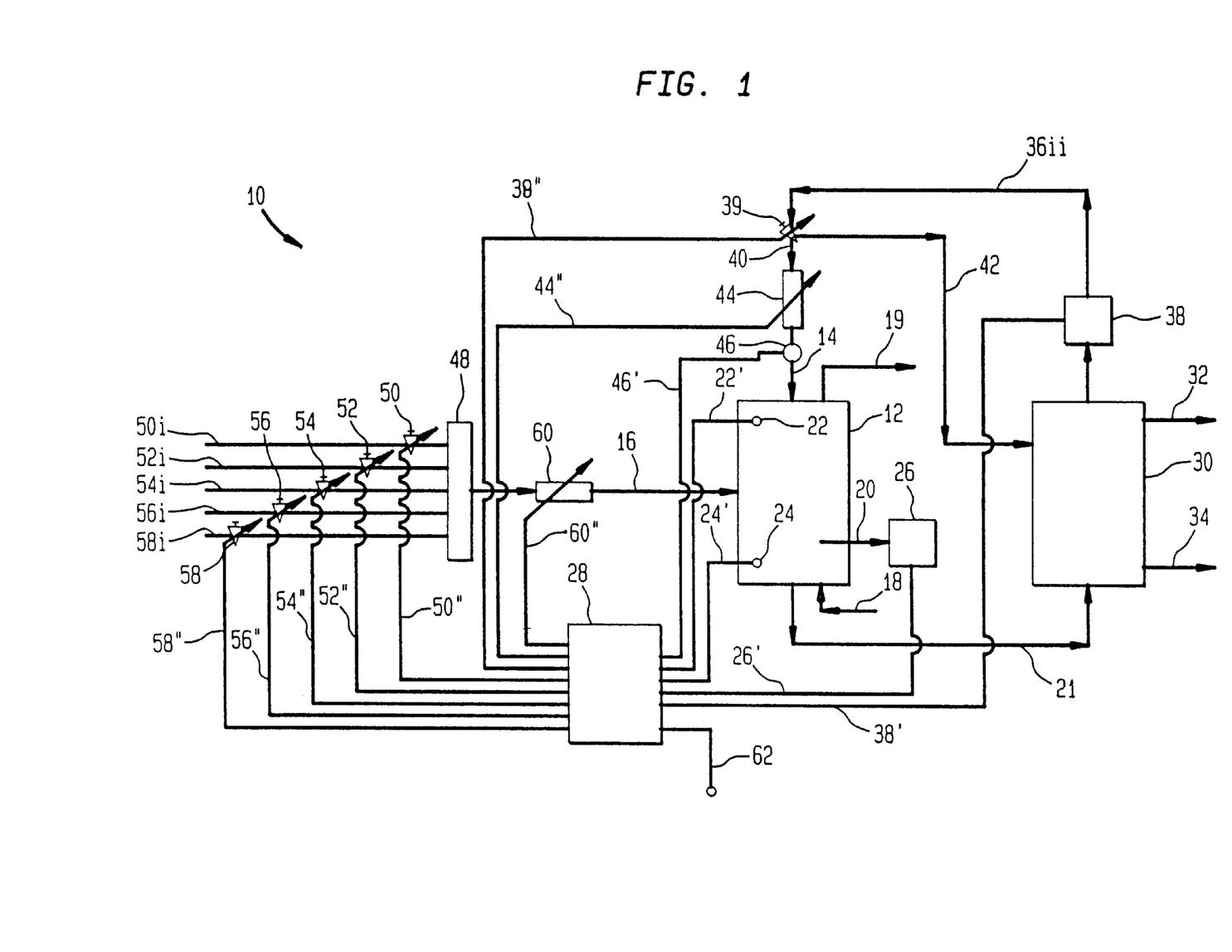
FIG. 1 illustrates schematically a preferred embodiment of the present invention.

A preferred embodiment of this invention is illustrated in FIG. 1. In FIG. 1, there is depicted a device or continuous reactor system 10 comprising a reaction chamber 12. A recycle feeding or inlet line 14, a new raw material feeding or inlet line 16, a gaseous oxidant feeding or inlet line 18, a gas outlet line 19, a sampling line 20, a predominantly non-gaseous outlet line 21, and means for measuring temperature, such as thermocouples 22 and 24 for example, are connected to the reaction chamber 12. Other elements, commonly used with reaction chambers, such as pressure monitors and controllers for example, and the like, although preferably utilized according to the instant invention, are not shown in FIG. 1 for purposes of clarity. Also, optional means for conducting chemical analysis of the contents of the reaction chamber 12 are not shown also for purposes of clarity.

The sampling line 20 leads to a phase analyzer 26, which provides liquid phase information to a computerized controller 28 through input line 26'. An example of phase analyzer will be described at a later point. The optional means (not shown) for conducting chemical analysis of the contents of the reaction chamber 12, preferably, also provide ingredient content information to the computerized controller 28. The inlet, outlet, input or output lines may be positioned in any suitable location of the reaction chamber 12. The words "inlet" and "outlet" are used for lines which feed or withdraw materials, respectively, while the words "input" and "output" are used for lines which provide information to the computerized controller 28, or are utilized by the controller to control other elements of the device, respectively.

The predominantly non-gas outlet line 21 leads to a material management station 30, at which the products of reaction, any by-products, non-converted raw materials, etc., are separated by well known to the art techniques. Such techniques may involve filtration, distillation, crystallization, other types of separation, evaporation, cooling, heating, storage, decontamination, incineration, disposal, etc.

The desired product of reaction follows product path 32, the non-recyclable by-products follow non-recyclables path 34, while recyclable materials follow recyclables line 36, which line 36 leads to an analytical apparatus 38 for analysis of the contents of the recyclables. The analytical apparatus 38 samples the recyclables for analysis and allows the major portion of said recyclables to enter line 36ii. Line 36 may comprise one or a plurality of lines, depending of the nature of the recyclables. Some of these lines may even circumvent the analytical apparatus 38, if so desired (if for example the content of the recyclable material under consideration is known or previously determined by any of well known to the art techniques).

The recyclables follow line 36ii, which leads to a three way valve 39, in a manner that the recyclables may follow line 40 or 42 or both in any desired ratio. Line 42 leads back to the material management station 30 for storage or retention or re-work, or the like, while line 40 leads to a first heat exchanger (including cooler or heater or the like) 44.

The 3 way valve 39 is controlled by the computerized controller 28 through output line 38". Similarly, the heat exchanger 44 is controlled by the computerized controller 28 through output line 44". Preferably one or more input lines (not shown for purposes of clarity) provide temperature information to the computerized controller 28 regarding the recyclables as they enter end exit the heat exchanger 44.

The recyclables enter the reaction chamber 12 after they pass through flowmeter 46, which gives recyclables flow data to the computerized controller 28 through input line 46'.

Input lines 22' and 24' feed the computerized controller 28 with temperature information within the reaction chamber 28. Both lines may be necessary, or only one, or more than two, depending on the information required in each particular case.

Flow regulation valves 50, 52, 54, 56, and 58 are connected to inlet lines 50i, 52i, 54i, 56i, and 58i, which provide hydrocarbon, solvent, catalyst, promoter, and other adjuncts, respectively, to a pre-mixing vessel 48. The premixing vessel 48 is preferably of small size and positioned in a way that all its contents are moving out of it and through line 16, so that if more than one phase is present, there is no accumulation of a particular phase in the pie-mixing vessel. Premixing vessel 48 is connected with a second heat exchanger (including cooler or heater or the like) 60, which in turn is connected to the reaction chamber 12. The inlet lines 50i, 52i, 54i, 56i, and 58i, may however be directly connected to the second heat exchanger 60 or to the reaction chamber 12.

Flow regulation valves 50, 52, 54, 56, and 58 are controlled by the computerized controller 28 through output lines 50", 52", 54", 56", and 58", respectively. A number of flowmeters (not shown for purposes of clarity) connected to lines 50i, 52i, 54i, 56i, and 58i, provide flow information regarding hydrocarbon, solvent, catalyst, promoter, and other adjuncts, to the computerized controller 28 through multiple input line 62.

The reaction chamber 12 may be heated or cooled by heating or cooling means (not shown) well known to the art.

The lines 14 and 16 may merge together into a single line (not shown), and feed the reaction chamber through said single line. The phase analyzer 26, or an additional phase analyzer (not shown) may also be connected to this single line, so that it detects the presence of a second phase qualitatively or quantitatively, even before the liquid enters the reaction chamber, and before the oxidation starts taking place. Preferably, the determination of the second phase takes place under the same temperature and pressure of the reaction (if the pressure is not excessive).

Figure 2:
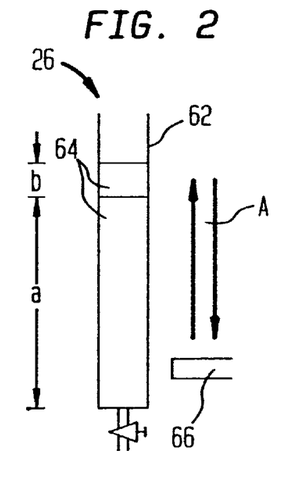
FIG. 2 illustrates schematically a phase analyzer, which may be utilized according to the present invention.

One example of the phase analyzer 26 is better illustrated in FIG. 2. It may comprise an at least partially transparent cell 62 for accepting liquid from the reaction chamber 12, and a detector 66 adapted to move up and down the height of the cell 62, in order to detect the presence of more than one liquid phases 64. The nature of the cell 62 is preferably such as to accept high pressures, preferably similar to the reaction pressures. The detector 66 can be a color detector, a refractive index detector, an ultrasonic detector, or in general, any type of detector that can distinguish and differentiate between liquids by using a property of the two liquids, which property may differentiate one from the other.

Figure 3:
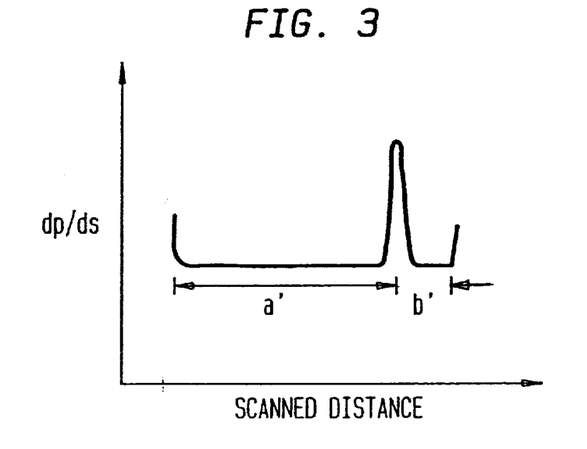
FIG. 3 illustrates the response of the phase analyzer of FIG. 2, when the detector scans the analyzer's cell, which contains two liquid phases.

If the phases separate to a lower phase having a height "a", and to an upper phase having a height "b", the differential of the detected property per scanned distance dp/ds ("p" being the property, such as color for example, and "s" being the scanning distance as shown by the arrows A) will give a graph as shown in FIG. 3, wherein a'/b'=a/b, from which the degree of second phase formation may be determined.

If the phases are difficult to separate into distinct portions, additional techniques to aid such separation may be utilized. Centrifuging, ultra-centrifuging, addition of flocculation agents, and the like, are example of such techniques.

Although in FIG. 2 the detector 66 is shown to reside outside the cell, it may very well reside inside the cell 62. A conductivity detector is an example of a detector that should come in contact with the liquid phases and preferably be inside the cell.

The detector may be a single detector traveling up and down the height of the cell, or otherwise scanning the cell, or it may be two or more detectors located steady at different positions of the cell. In the case of using two detectors, it is preferable to arrange one detector in the vicinity of the bottom of the cell and one detector in the vicinity of the top of the cell. It is obvious that in the case of relative movement of the detector with respect to the cell, the cell may be the moving element and the detector the steady element. Instead of utilizing a detector, an observer may visually detect the levels of the two liquids and provide this information to the computerized controller 28.

The phase detector may also be based on measuring or detecting the turbidity (cloudiness) of the mixture of one phase dispersed in the other phase, since the two phases, for all practical purposes and substantially always, will have different indices of refraction. A single liquid phase will be clear, but a second phase dispersed in another phase will produce a turbid mixture. Care will have to be taken in this case to filter out any solid matter before determination of the turbidity. Incident light from an angle may also be used to help scattering and detection of a finely dispersed second phase into a first phase.

The temperature at which the cell 62 and its contents are subjected to, may be ambient temperature in the range of 20 to 25° C., any other temperature, or preferably the same temperature as the first temperature, which is the reaction temperature in the reaction chamber 12 in a zone that the reaction occurs (reaction zone). Depending on the temperature at which the cell 62 operates it may have to also be under pressurized conditions and closed to maintain its contents in the liquid state.

In operation of this embodiment, hydrocarbon, solvent, catalyst, promoter and any other desired adjuncts are added to the pre-mixing vessel 48, where they are mixed together. The pre-mixing vessel is small enough and positioned in a manner that if there is phase separation, no particular phase remains behind, but all phases are commingled and they proceed through the second heat exchanger 60 and to the reaction chamber 12 through line 16. The feed rates of the new raw materials fed through lines 50i, 52i, 54i, 56i, and 58i depend on the feed rates of the recyclables fed to the reaction chamber 12 through recycle feeding line 14. Information regarding the analytical results from the analytical apparatus 38 is provided to the computerized controller 28, which combines this information with the information from the flowmeter 46 and the information from the flowmeters (not shown) of lines 50i, 52i, 54i, 56i, and 58i, and calculates the total feed rate of each individual ingredient entering the reaction chamber 12.

The computerized controller preferably gives precedence to the recyclables, and then it adjusts each of the valves 50, 52, 54, 56, and 58 through output lines 50", 52", 54", 56", and 58", respectively, in a manner that the total feed rate of each individual ingredient entering the reaction chamber 12 has a desired value. The desired value of each ingredient feed rate is preferably adjusted toward formation and maintenance of a single phase at the reaction temperature, otherwise called the first temperature.

Of course, when the operation starts, there are no recyclable materials, so that only new raw materials start entering the system through one or more of lines 50i, 52i, 54i, 56i, and 58i, and finally enter the reaction chamber 12 through line 16. During starting the operation, the different feed rates of new raw materials are arranged so that a single phase exists at the first temperature. When talking about a single or multiple phase in this description, the inventors mean single or multiple liquid phases. When the inventors want to refer to a solid phase, they specifically refer to a solid phase.

The balance of materials is also preferably arranged to be such that when water starts being formed during the oxidation, no second phase is formed. The amount of water formed depends on the conversion taking place when the system attains a steady state. The more solvent, acetic acid for example, is present at this steady state, the more water may be withstood by the system without formation of a second phase. Since the formation of water is substantially unavoidable when a hydrocarbon is oxidized, and in some respects its presence may even be desirable (for at least partial hydrolysis of undesirable ester by-products, for example), it is preferable to work at a steady state which can contain at least a predetermined content of water without the formation of a second phase. Removal of water in any step of the process, if necessary or desired, may be achieved by a number of ways, including for example distillation, addition of acid anhydrides, and other well known to the art methods.

The more hydrocarbon, cyclohexane for example, is present in the reaction chamber the higher the potential of formation of a second phase. At the same time, if too little hydrocarbon is present, the reaction starts starving from lack of hydrocarbon. According to the instant invention, the amount of hydrocarbon present in the steady state is preferably just above the point at which starvation is observed. "Just above" starvation means preferably between 0 to 20% above starvation, and more preferably 5 to 20% above starvation.

At the same time that the above mentioned ingredients enter the reaction chamber 12, a gas containing an oxidant, preferably oxygen, enter the reaction chamber through the gaseous oxidant feeding line 18, and it comes in contact with the mixture containing the hydrocarbon.

The reaction temperature or first temperature is monitored by one or more thermocouples, such as thermocouples 22 and 24, for example, which provide temperature information to the controller 28.

The computerized controller 28, based on this temperature information adjusts the first and second heat exchangers through output lines 44" and 60", respectively, in a manner that in combination with the heat released by the reaction, and the thermal characteristics of the reaction chamber 12, the first temperature attains and maintains a desired value. In order to lower the temperature in the reaction chamber, the heat exchangers are adjusted to lower the temperatures in lines 14 and 16. In addition to or instead of this, the reaction chamber itself may be provided with heating and/or cooling means (not shown for purposes of clarity, but well known to the art), controlled by the computerized controller 28, so that the temperature attains and maintains the desired value. The desired value may, of course, be a desired range of values.

As the reaction or first temperature is raised, the potential for formation of a single phase is increased, and the rate of reaction is increased. However, the selectivity to the desired final product may suffer. Therefore, a balance among rate of reaction, selectivity, and reaction or first temperature has to be decided. This decision may depend on the particular circumstances, and may be based on economical, safety, environmental, and other considerations.

Thus, the temperature may be adjusted through the computerized controller 28 within the desired range in a manner to promote the formation and/or maintenance of a single phase. If a single phase already exists, the temperature may preferably be reduced to the minimum limit of the desired range, and maintained there, if this decrease in temperature does not cause the formation of a second phase.

Lowering the pressure within the reaction chamber 12 moves the system toward a single phase formation since more hydrocarbon, cyclohexane for example, evaporates and the content of hydrocarbon in the liquid decreases. If inert gases are present in the gaseous oxidant (if the gaseous oxidant is predominantly a mixture of oxygen and nitrogen, for example), it is preferable that the relative pressure of oxidant, oxygen for example, is maintained constant during lowering the total pressure.

Increasing sparging in the case of a stirred-tank reaction chamber, or in general the flow of the gaseous oxidant in the case of an atomization reactor (described for example in our aforementioned patent and patent applications) has a similar effect as lowering the pressure.

Lowering the conversion, or hold-up time in the reaction chamber 12, decreases the amount of water formed, which has as an effect to promote the formation of a single phase, and at the same time it decreases the amount of the acid formed, predominantly adipic acid, for example, in the oxidation of cyclohexane, which decrease promotes also the formation of a single phase.

Lowering the amount of catalyst, cobalt acetate for example, also promotes the formation of a single phase. It should be noted here that when cobaltous acetate tetrahydrate is used, water is necessarily introduced, corresponding to the water of hydration of the cobaltous acetate salt.

If the formation of a second phase is detected by the phase detector 26, the detector 26 transfers such information to the computerized controller 28 through input line 26'. The computerized controller 28 in turn takes steps toward reformation again of a single phase in the reaction chamber 12, by ordering one or more of the elements that it controls to function in a manner directed toward the reformation of the single phase, as described above. Although, depending on the particular circumstances, the functioning or activation of the miscellaneous elements controlled by the computerized controller 28 may be arranged in any desired precedence order, it is preferable in most occasions, according to the present invention, to be arranged as follows:

For stirred-tank reactors, when detection of formation of a second phase is detected at the same temperature as the temperature prevailing in the reaction zone, the computerized controller gives precedence to decreasing the feed rate of the hydrocarbon by stepwise closing valve 50 through output line 50". The steps are preferably between 1 to 60% of the feed rate at the time that the formation of the second phase was detected, more preferably 1 to 30%, and even more preferably 2 to 10%. A predetermined time (preferably ½ to 10 minutes, and more preferably 1 to 2 minutes) after each step, a sample is taken again through line 20 to the phase analyzer, where it is examined, and the results are provided to the computerized controller 28. If a single phase has been reformed, no further action is taken. If a single phase has not been formed the same process may be repeated.

If for some reason water is fed to the system through line 58i, the computerized controller 28 gives second precedence to valve 58 through output line 58", an a similar procedure as above is followed. This step, however, may assume first precedence in case that the amount of cyclohexane fed to the reaction chamber 12 moves below a point at which the reaction starts starving because of lack of adequate hydrocarbon, such as cyclohexane for example.

Figure 4:
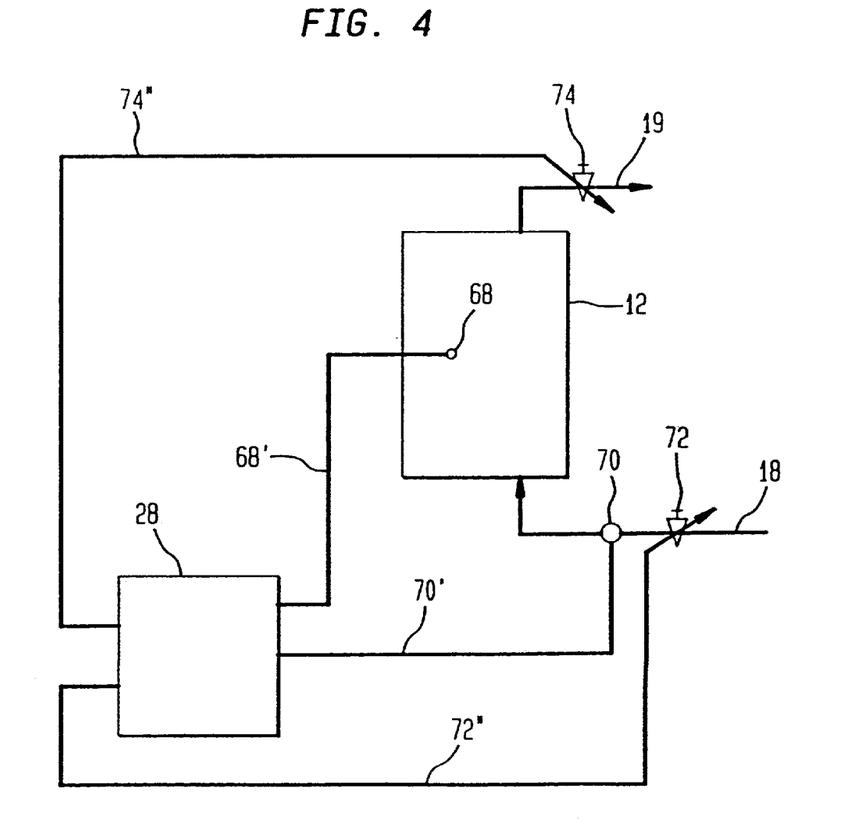
FIG. 4 shows the elements related to the pressure and the gaseous oxidant flow rate controls.

The next or third precedence is given to the rate of gaseous oxidant flow through line 18, which is also regulated (not shown in FIG. 1 for purposes of clarity) by the computerized controller 28, as better shown in FIG. 4, wherein the majority of the elements is not shown. FIG. 4 shows the elements related to the pressure and the gaseous oxidant flow rate controls. The reaction chamber 12 is provided with a pressure monitor 68, which transmits pressure information to the computerized controller 28 through input line 68'. The gaseous oxidant feeding line is provided with a flowmeter 70, which provides flow rate information to the computerized controller 12 through input line 70'. The computerized controller 28 controls valve 72 on the gaseous oxidant feeding line and valve 74 on the gas outlet line 19 through output lines 72" and 74".

If the above described steps are not adequate to eliminate the second phase, and provide a single phase, the computerized controller 28 opens the valve 72 in a manner that the flow increases stepwise from the value that it had to a higher value. The steps or increments of increase are preferably between 1 to 60% of the feed rate at the time that the formation of the second phase was detected, more preferably 1 to 30%, and even more preferably 2 to 10%. As in the previous cases, a predetermined time (preferably ½ to 10 minutes, and more preferably 1 to 2 minutes) after each step, a sample is taken again through line 20 to the phase analyzer, where it is examined, and the results are provided to the computerized controller 28. If a single phase has been reformed, no further action is taken. If a single phase has not been formed the same process may be repeated. In order to keep the pressure within the reaction chamber constant, valve 74 is also opened accordingly, so that the pressure as detected by the pressure monitor 68 does not increase.

The next or fourth precedence is given to pressure within the reaction chamber 12. If the above described steps are not adequate to eliminate the second phase, and provide a single phase, the computerized controller 28 closes further the valve 72 and opens further the valve 74 in a manner that the pressure decreases stepwise from the value that it had to a lower value. The steps or increments of pressure decrease are preferably between 5 to 30% of the pressure at the time that the formation of the second phase was detected, more preferably 5 to 20%, and even more preferably 10 to 20%. As in the previous cases, a predetermined time (preferably ½ to 10 minutes, and more preferably 1 to 2 minutes) after each step, a sample is taken again through line to the phase analyzer, where it is examined, and the results are provided to the computerized controller 28. If a single phase has been reformed, no further action is taken. If a single phase has not been formed the same process is repeated. In order to keep the partial pressure of the oxidant constant, which is a preferred mode of operation, oxidant, such as oxygen for example, may be added through an additional port (not shown).

The computerized controller gives fifth precedence to increasing the feed rate of the solvent, acetic acid for example, by stepwise opening further valve 52 through output line 52". The steps are preferably between 1 to 60% of the initial feed rate, more preferably 1 to 30%, and even more preferably 2 to 10%. A predetermined time (preferably ½ to 10 minutes, and more preferably 1 to 2 minutes) after each step, a sample is taken again through line 20 to the phase analyzer, where it is examined, and the results are provided to the computerized controller 28. If a single phase has been reformed, no further action is taken. If a single phase has not been formed the same process may be repeated.

The computerized controller gives sixth precedence to decreasing conversion or increasing the feed rate of all entering raw materials, excluding catalyst, and the rate of the outgoing products through the predominantly non-gas outlet line 21, all in a proportional manner. This increase is conducted stepwise by further opening all involved valves, in a manner to increase all feeds and outgoing product flows proportionally to each other. The steps are preferably as in other cases between 1 to 60% of the initial feed rates and outgoing flows, more preferably 1 to 30%, and even more preferably 2 to 10%. A predetermined time (preferably ½ to 10 minutes, and more preferably 1 to 2 minutes) after each step, a sample is taken again through line 20 to the phase analyzer, where it is examined, and the results are provided to the computerized controller 28. If a single phase has been reformed, no further action is taken. If a single phase has not been formed the same process may be repeated.

Seventh precedence is given to the temperature, with increases allowed only within a predetermined region as described earlier.

Eighth precedence is given to decreasing the feed rate of catalyst.

In the above description of precedence for attaining and maintaining a single phase within the reaction zone, mention was made only to the valves for introducing new raw materials. It should be understood, however, that this would be preferably conducted in combination with the control of the recyclables from information received from the analytical apparatus 38 through input line 38', and from the flowmeter 46, by adjusting flow through valve 39 and the temperature through heat exchanger 44.

In the case of atomization reactors, temperature control for attaining and maintaining a single phase would take at least third precedence.

It should also be pointed out that a combination from different preference levels may be utilized before a multi-step process at each level of precedence. For example, the computerized controller may be programmed to perform only one step or a predetermined number of steps in each precedence level, the number of steps being the same or different at each particular level. Also, the computerized controller may be programmed to change the precedence levels, depending on any particular circumstances.

A preferable type of computerized controller comprises a "learning computer" or a "neuro-computer", the functionality of which is known to the art, and which collects information from different places of the device (for example pressure, temperature, chemical or other analysis, etc.), stores this information along with the result (reaction rate, for example), and it is programmed to use this information in the future, along with other data if applicable, to make decisions regarding the action to be taken (for example regarding precedence, steps within precedence, etc.) at each instance.

Although the miscellaneous functions are preferably controlled by the computerized controller 28, it is possible, according to this invention, to utilize manual controls for controlling one or more functions.

If the phase analyzer is at ambient temperature, correlations can be made between the analytical results and the ratio of RT polar phase to RT non-polar phase. If the ratio is small with substantially all catalyst in the RT polar phase, solvent should be added in adequate amounts to a ratio of solvent to hydrocarbon of preferably higher than 0.5, and more preferably between 0.5 and 1 at water levels preferably lower than 5%. All ratios in this discussion are by weight, unless otherwise stated.

As aforementioned, the methods of the instant invention may also comprise a step of correlating phase diagram data with variables selected from a group consisting of temperature in the reaction zone, pressure in the reaction zone, rate of gaseous oxidant flow, water feed rate, catalyst feed rate, hydrocarbon feed rate, solvent feed rate, and a combination thereof, in order to control the oxidation of the hydrocarbon by preferably controlling in the reaction zone a variable selected from a group consisting of temperature in the reaction zone, pressure in the reaction zone, rate of gaseous oxidant flow, water feed rate, catalyst feed rate, hydrocarbon feed rate, solvent feed rate, and a combination thereof.

Figure 5:
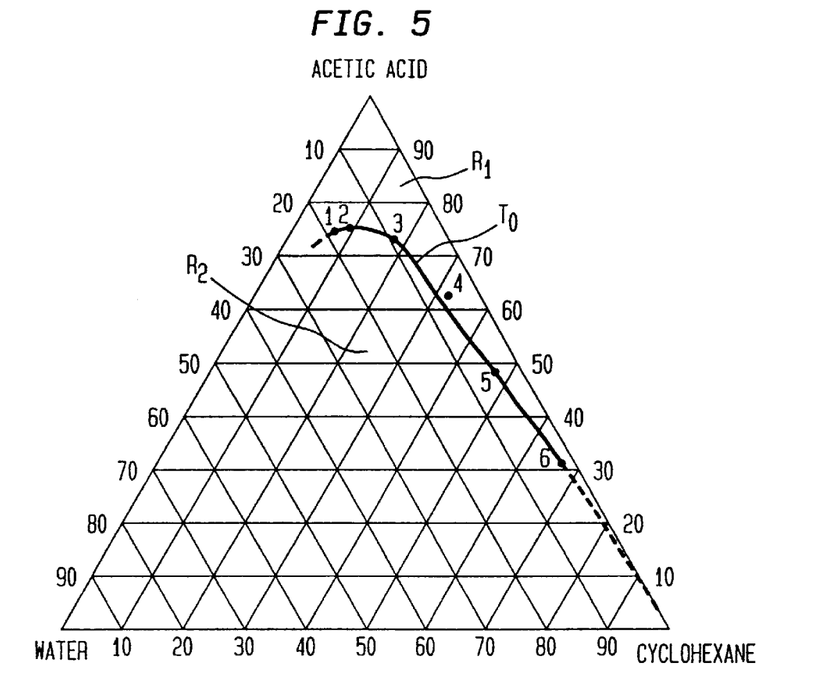
FIG. 5 shows a ternary phase diagram of (Acetic Acid)/(Cyclohexane)/(Water) at 100° C. at 0% level of cobalt acetate tetrahydrate.
Figure 6:
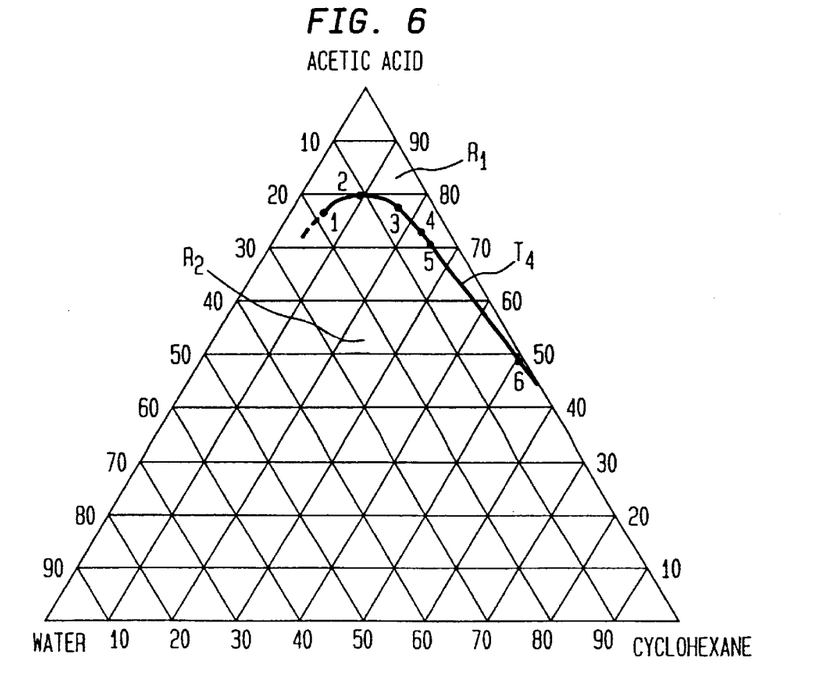
FIG. 6 shows a ternary phase diagram of (Acetic Acid)/(Cyclohexane)/(Water) at 100° C. at 4% level of cobalt acetate tetrahydrate.

An example of such a ternary phase diagram of (Acetic Acid)/(Cyclohexane)/(Water) at 100° C., at a catalyst level of 0%, is shown in FIG. 5, wherein the one phase $R_1$ and two phase $R_2$ regions are separated by the transition line $T_0$. The one phase region $R_1$ is above the transition line To, while the two phase region $R_2$ is under the transition line $T_0$. Another example of such a ternary phase diagram of (Acetic Acid)/(Cyclohexane)/(Water) at 10° C., at a level of 4% catalyst is shown in FIG. 6, wherein the one phase $R_1$ and two phase $R_2$ regions are separated by the transition line $T_4$. The one phase region $R_1$ is above the transition line $T_4$, while the two phase region $R_2$ is under the transition line $T_4$.

As it can be seen, the presence of catalyst, cobalt acetate tetrahydrate in this case, suppresses the one phase region to a certain degree. Presence of adipic acid in the mixture of components does not substantially move the transition curve. Ternary diagrams for different levels of catalyst, temperature, and/or other components, which may have influence on the transition curves may be created very easily, preferably experimentally. Thermodynamic data bases and computer flow-sheet simulation programs, for example, may be used as guidelines to determine the approximate position of the transition curve, which can then be refined and defined more accurately by limited experimentation. One easy way to construct an experimental ternary diagram for a given catalyst level, temperature, etc., is for example, to select different positions in the one phase region of the theoretical diagram close to the theoretical transition curve, and start adding water until a second phase is formed. This will define an experimental point on the experimental transition curve for the given catalyst level, temperature, etc. The exact compositions of the different experimental points in the diagrams shown in FIGS. 5 and 6 are listed in Tables 4 and 5, respectively. Points to the left of point 1 are omitted because the amount of cyclohexane involved is too small for most practical purposes.

TABLE 4

Compositions defining transition curve $T_0$ in FIG. 5

Experimental Data

| | Components | Amount | wt % | | Amount | wt % |
|---|---|---|---|---|---|---|
| 1 | Acetic Acid | 15.105 | 75.70 | 2 | 15.586 | 77.93 |
| | Water | 3.750 | 18.79 | | 2.646 | 13.23 |
| | Cyclohexane | 1.099 | 5.51 | | 1.768 | 8.84 |
| | Total | 19.954 | | | 20.000 | |
| 3 | Acetic Acid | 15.124 | 75.27 | 4 | 12.005 | 62.18 |
| | Water | 1.762 | 8.77 | | 0.895 | 4.64 |
| | Cyclohexane | 3.207 | 15.96 | | 6.408 | 33.19 |
| | Total | 20.093 | | | 19.308 | |
| 5 | Acetic Acid | 9.859 | 48.30 | 6 | 6.550 | 32.75 |
| | Water | 0.537 | 2.63 | | 0.140 | 0.70 |
| | Cyclohexane | 10.018 | 49.08 | | 13.310 | 66.55 |
| | Total | 20.411 | | | 20.000 | |

TABLE 5

Compositions Defining Transition Curve $T_4$ in FIG. 6

| | | With 4 wt % Catalyst | | Catalyst free basis | |
|---|---|---|---|---|---|
| | Components | Amount | wt % | Amount | wt % |
| 1 | Acetic Acid | 15.198 | 72.88 | 15.198 | 75.95 |
| | Cyclohexane | 1.000 | 4.80 | 1.000 | 5.00 |
| | Catalyst | 0.844 | 4.05 | 0.000 | 0.00 |
| | Water | 3.812 | 18.28 | 3.812 | 19.05 |
| | Total | 20.854 | | 20.010 | |
| 2 | Acetic Acid | 17.000 | 76.08 | 17.000 | 79.07 |
| | Cyclohexane | 2.000 | 8.95 | 2.000 | 9.30 |
| | Catalyst | 0.844 | 3.78 | 0.000 | 0.00 |
| | Water | 2.500 | 11.19 | 2.500 | 11.63 |
| | Total | 22.344 | | 21.500 | |
| 3 | Acetic Acid | 14.762 | 72.56 | 14.762 | 77.08 |
| | Cyclohexane | 3.129 | 15.38 | 3.129 | 16.34 |

TABLE 5-continued

Compositions Defining Transition Curve $T_4$ in FIG. 6

| | Components | With 4 wt % Catalyst Amount | wt % | Catalyst free basis Amount | wt % |
|---|---|---|---|---|---|
| | Catalyst | 0.812 | 3.99 | 0.000 | 0.00 |
| | Water | 1.261 | 6.20 | 1.261 | 6.59 |
| | Total | 20.344 | | 19.152 | |
| 4 | Acetic Acid | 12.603 | 69.46 | 12.603 | 72.66 |
| | Cyclohexane | 3.843 | 21.18 | 3.843 | 22.16 |
| | Catalyst | 0.799 | 4.40 | 0.000 | 0.00 |
| | Water | 0.899 | 4.95 | 0.899 | 5.18 |
| | Total | 18.144 | | 17.345 | |
| 5 | Acetic Acid | 13.606 | 67.68 | 13.606 | 70.48 |
| | Cyclohexane | 4.807 | 23.91 | 4.807 | 24.90 |
| | Catalyst | 0.798 | 3.97 | 0.000 | 0.00 |
| | Water | 0.893 | 4.44 | 0.893 | 4.63 |
| | Total | 20.104 | | 19.306 | |
| 6 | Acetic Acid | 9.799 | 47.25 | 9.799 | 49.22 |
| | Cyclohexane | 10.004 | 48.24 | 10.004 | 50.25 |
| | Catalyst | 0.831 | 4.01 | 0.000 | 0.00 |
| | Water | 0.106 | 0.51 | 0.106 | 0.53 |
| | Total | 20.740 | | 19.909 | |

When such diagrams are used by the controller to operate the system and ensure that the reaction is conducted in one phase, analysis of the contents of the reaction chamber may be performed, preferably by Gas and Liquid Chromatography, and the flow rates of the different feeds (including recycled matter) may be changed accordingly to produce mixtures characterized by one phase. A similar procedure may be followed from diagrams produced at different temperatures, so that temperature manipulations may produce the desired results. Thus, for example, miscellaneous parameters may be changed to achieve the one phase desired condition, including but not limited to temperature in the reaction zone, pressure in the reaction zone, rate of gaseous oxidant flow, water feed rate, catalyst feed rate, hydrocarbon feed rate, solvent feed rate, and a combination thereof.

Diacids (for example adipic acid, phthalic acid, isophthalic acid, terephthalic acid, and the like) or other suitable compounds may be reacted, according to well known to the art techniques, with a third reactant selected from a group consisting of a polyol, a polyamine, and a polyamide in a manner to form a polymer of a polyester, or a polyamide, or a (polyimide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by well known to the art techniques to form fibers.

Oxidations according to this invention, are non-destructive oxidations, wherein the oxidation product is different than carbon monoxide, carbon dioxide, and a mixture thereof. Of course, small amounts of these compounds may be formed along with the oxidation product, which may be one product or a mixture of products.

Examples include, but of course, are not limited to preparation of $C_5$–$C_8$ aliphatic dibasic acids from the corresponding saturated cycloaliphatic hydrocarbons, such as for example preparation of adipic acid from cyclohexane;

preparation of $C_5$–$C_8$ aliphatic dibasic acids from the corresponding ketones, alcohols, and hydroperoxides of saturated cycloaliphatic hydrocarbons, such as for example preparation of adipic acid from cyclohexanone, cyclohexanol, and cyclohexylhydroperoxide;

preparation of $C_5$–$C_8$ cyclic ketones, alcohols, and hydroperoxides from the corresponding saturated cycloaliphatic hydrocarbons, such as for example preparation of cyclohexanone, cyclohexanol, and cyclohexylhydroperoxide from cyclohexane; and preparation of aromatic multi-acids from the corresponding multi-alkyl aromatic compounds, such as for example preparation of phthalic acid, isophthalic acid, and terephthalic acid from o-xylene, m-xylene and p-xylene, respectively.

Regarding adipic acid, the preparation of which is especially suited to the methods and apparatuses of this invention, general information may be found in a plethora of U.S. Patents, among other references. These, include, but are not limited to:

U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); 4,263,453; 4,331,608; 4,606,863; 4,902,827; 5,221,800; and 5,321,157.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of this invention.

All explanations given hereinabove are to be considered as speculative and should not be construed as limiting the breadth of the claims.

What is claimed is:

1. A method of controlling in a reaction zone the oxidation of a hydrocarbon to form an acid in the presence of a catalyst, a solvent, an optional promoter, and oxidation products including water, the hydrocarbon, the catalyst, the solvent, and at least part of the oxidation products including water forming at least partially a liquid mixture, the method comprising the steps of:

(a) bringing in contact the liquid mixture with a gaseous oxidant in the reaction zone at a first temperature, the first temperature being adequately high for the oxidation to proceed;

(b) periodically obtaining phase information regarding the reaction; and (c) making phase-related adjustments to the liquid mixture, the phase-related adjustments being at least partially based on phase formation relationships when said liquid mixture is at a second temperature, and being directed toward formation and maintenance of a single liquid phase at the first temperature.

2. A method as defined in claim 1, wherein the first and the second temperatures are substantially the same.

3. A method as defined in claim 1, wherein the second temperature is substantially ambient temperature in the range of about 20° to 25° C.

4. A method as defined in claim 2, wherein the phase related adjustments to the liquid mixture are directed toward formation and maintenance of a single liquid phase at the first temperature.

5. A method as defined in claim 3, wherein the phase related adjustments to the liquid mixture are directed toward formation and maintenance of a single liquid phase at the first temperature.

6. A method as defined in claim 1, wherein the phase related adjustments to the liquid mixture are conducted by controlling in the reaction zone a variable selected from a group consisting of temperature in the reaction zone, pressure in the reaction zone, rate of gaseous oxidant flow, water feed rate, catalyst feed rate, hydrocarbon feed rate, solvent feed rate, and a combination thereof.

7. A method as defined in claim 4, wherein the phase related adjustments to the liquid mixture are conducted by controlling in the reaction zone a variable selected from a group consisting of temperature in the reaction zone, pressure in the reaction zone, rate of gaseous oxidant flow, water feed rate, catalyst feed rate, hydrocarbon feed rate, solvent feed rate, and a combination thereof.

8. A method as defined in claim 5, wherein the phase related adjustments to the liquid mixture are conducted by controlling in the reaction zone a variable selected from a group consisting of temperature in the reaction zone, pressure in the reaction zone, rate of gaseous oxidant flow, water feed rate, catalyst feed rate, hydrocarbon feed rate, solvent feed rate, and a combination thereof.

9. A method as defined in claim 1, wherein the hydrocarbon is a cyclic aliphatic hydrocarbon.

10. A method as defined in claim 9, wherein the cyclic aliphatic hydrocarbon has 5 to 12 carbon atoms.

11. A method as defined in claim 10, wherein the cyclic aliphatic hydrocarbon comprises cyclohexane.

12. A method as defined in claim 11, wherein the gaseous oxidant comprises oxygen.

13. A method as defined in claim 12, wherein the solvent comprises acetic acid.

14. A method as defined in claim 13, wherein the catalyst comprises cobalt ions.

15. A method as defined in claim 14, wherein the promoter comprises acetaldehyde.

16. A method as defined in claim 4, wherein the hydrocarbon comprises cyclohexane, the solvent comprises acetic acid, the catalyst comprises cobalt ions, and the oxidation products comprise adipic acid and water.

17. A method as defined in claim 5, wherein the hydrocarbon comprises cyclohexane, the solvent comprises acetic acid, the catalyst comprises cobalt ions, and the oxidation products comprise adipic acid and water.

18. A method as defined in claim 6, wherein the hydrocarbon comprises cyclohexane, the solvent comprises acetic acid, the catalyst comprises cobalt ions, and the oxidation products comprise adipic acid and water.

19. A method as defined in claim 7, wherein the hydrocarbon comprises cyclohexane, the solvent comprises acetic acid, the catalyst comprises cobalt ions, and the oxidation products comprise adipic acid and water.

20. A method as defined in claim 8, wherein the hydrocarbon comprises cyclohexane, the solvent comprises acetic acid, the catalyst comprises cobalt ions, and the oxidation products comprise adipic acid and water.

21. A method as defined in claim 1, wherein the hydrocarbon is a methylated aromatic hydrocarbon.

22. A method as defined in claim 21, wherein the methylated aromatic hydrocarbon comprises toluene and the acid comprises benzoic acid.

23. A method as defined in claim 22, wherein the gaseous oxidant comprises oxygen.

24. A method as defined in claim 21, wherein the methylated aromatic hydrocarbon is selected from a group consisting of o-xylene, m-xylene, p-xylene, and a mixture thereof, and the acid is selected from a group consisting of phthalic acid, isophthalic acid, terephthalic acid, and a mixture thereof.

25. A method as defined in claim 24, wherein the gaseous oxidant comprises oxygen.

26. A method as defined in claim 1, wherein hydrocarbon is a methylated aromatic hydrocarbon selected from a group consisting of o-xylene, m-xylene, p-xylene, and a mixture thereof, and the acid is selected from a group consisting of phthalic acid, isophthalic acid, terephthalic acid, and a mixture thereof.

27. A method as defined in claim 5, wherein hydrocarbon is a methylated aromatic hydrocarbon selected from a group consisting of o-xylene, m-xylene, p-xylene, and a mixture thereof, and the acid is selected from a group consisting of phthalic acid, isophthalic acid, terephthalic acid, and a mixture thereof.

28. A method as defined in claim 6, wherein hydrocarbon is a methylated aromatic hydrocarbon selected from a group consisting of o-xylene, m-xylene, p-xylene, and a mixture thereof, and the acid is selected from a group consisting of phthalic acid, isophthalic acid, terephthalic acid, and a mixture thereof.

29. A method as defined in claim 7, wherein hydrocarbon is a methylated aromatic hydrocarbon selected from a group consisting of o-xylene, m-xylene, p-xylene, and a mixture thereof, and the acid is selected from a group consisting of phthalic acid, isophthalic acid, terephthalic acid, and a mixture thereof.

30. A method as defined in claim 8, wherein hydrocarbon is a methylated aromatic hydrocarbon selected from a group consisting of o-xylene, m-xylene, p-xylene, and a mixture thereof, and the acid is selected from a group consisting of phthalic acid, isophthalic acid, terephthalic acid, and a mixture thereof.

31. A method as defined in claim 1, wherein the phase related adjustments are conducted by controlling the first temperature.

32. A method as defined in claim 4, wherein the phase related adjustments are conducted by controlling the first temperature.

33. A method as defined in claim 5, wherein the phase related adjustments are conducted by controlling the first temperature.

34. A method as defined in claim 1, further comprising a step of atomizing the liquid mixture.

35. A method as defined in claim 2, further comprising a step of atomizing the liquid mixture.

36. A method as defined in claim 7, further comprising a step of atomizing the liquid mixture.

37. A method as defined in claim 16, further comprising a step of atomizing the liquid mixture.

38. A method as defined in claim 25, further comprising a step of atomizing the liquid mixture.

39. A method as defined in claim 27, further comprising a step of atomizing the liquid mixture.

40. A method as defined in claim 1, further comprising a step of stirring the liquid mixture.

41. A method as defined in claim 2, further comprising a step of stirring the liquid mixture.

42. A method as defined in claim 8, further comprising a step of stirring the liquid mixture.

43. A method as defined in claim 16, further comprising a step of stirring the liquid mixture.

44. A method as defined in claim 21, further comprising a step of stirring the liquid mixture.

45. A method as defined in claim 25, further comprising a step of stirring the liquid mixture.

46. A method as defined in claim 27, further comprising a step of stirring the liquid mixture.

47. A method as defined in claim 1, further comprising a step of correlating phase diagram data with variables selected from a group consisting of temperature in the reaction zone, pressure in the reaction zone, rate of gaseous oxidant flow, water feed rate, catalyst feed rate, hydrocarbon feed rate, solvent feed rate, and a combination thereof in order to control the oxidation of the hydrocarbon.

48. A method as defined in claim 2, further comprising a step of correlating phase diagram data with variables selected from a group consisting of temperature in the reaction zone, pressure in the reaction zone rate of gaseous oxidant flow, water feed rate, catalyst feed rate, hydrocarbon feed rate, solvent feed rate, and a combination thereof, in order to control the oxidation of the hydrocarbon.

49. A method as defined in claim 4, further comprising a step of correlating phase diagram data with variables selected from a group consisting of temperature in the reaction zone, pressure in the reaction zone, rate of gaseous oxidant flow, water feed rate, catalyst feed rate, hydrocarbon feed rate, solvent feed rate, and a combination thereof, in order to control the oxidation of the hydrocarbon.

50. A method as defined in claim 1, further comprising a step of correlating phase diagram data with variables selected from a group consisting of temperature in the reaction zone, pressure in the reaction zone, rate of gaseous oxidant flow, water feed rate, catalyst feed rate, hydrocarbon feed rate, solvent feed rate, and a combination thereof, in order to control the oxidation of the hydrocarbon.

51. A method as defined in claim 16, further comprising a step of correlating phase diagram data with variables selected from a group consisting of temperature in the reaction zone, pressure in the reaction zone., rate of gaseous oxidant flow, water feed rate, catalyst feed rate, hydrocarbon feed rate, solvent feed rate, and a combination thereof, in order to control the oxidation of the hydrocarbon.

52. A method as defined in claim 27, further comprising a step of correlating phase diagram data with variables selected from a group consisting of temperature in the reaction zone, pressure in the reaction zone, rate of gaseous oxidant flow, water feed rate, catalyst feed rate, hydrocarbon feed rate, solvent feed rate, and a combination thereof, in order to control the oxidation of the hydrocarbon.

53. A method as defined in claim 16, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively.

54. A method as defined in claim 53, further comprising a step of spinning the polymer into fibers.

55. A method as defined in claim 18, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively.

56. A method as defined in claim 55, further comprising a step of spinning the polymer into fibers.

57. A method as defined in claim 24, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

58. A method as defined in claim 57, further comprising a step of spinning the polymer into fibers.

59. A method as defined in claim 26, further comprising a step of reacting the acid with a reactant selected from a group consisting of polyol, a polyamine, and a polyamide in a manner to form a polymer of a polyester, or a polyamide, or a (polyimide and/or polyamideimide), respectively.

60. A method as defined in claim 59, further comprising a step of spinning the polymer into fibers.

61. A method of controlling in a reaction zone the oxidation of a hydrocarbon consisting substantially of cyclohexane to form adipic acid in the presence of a catalyst, a solvent consisting substantially of acetic acid, an optional promoter, and oxidation products including water, the cyclohexane, the catalyst, the acetic acid, and at least part of the oxidation products including water forming at least partially a liquid mixture, the method comprising the steps of:

(a) bringing in contact the liquid mixture with oxygen in the reaction zone at a first temperature, the first temperature being adequately high for the oxidation to proceed; and (b) periodically obtaining phase information regarding the reaction; and (c) making phase-related adjustments to the liquid mixture, the phase-related adjustments being at least partially based on phase formation relationships when said liquid mixture is at a second temperature, and being directed toward formation and maintenance of a single liquid phase at the first temperature.

62. A method as defined in claim 61, wherein the phase related adjustments to the liquid mixture are conducted by controlling in the reaction zone a variable selected from a group consisting of temperature in the reaction zone, pressure in the reaction zone, rate of gaseous oxidant flow, water feed rate, catalyst feed rate, hydrocarbon feed rate, solvent feed rate, and a combination thereof.

63. A method as defined in claim 61, further comprising a step of correlating phase diagram data with variables selected from a group consisting of temperature in the reaction zone, pressure in the reaction zone, rate of gaseous oxidant flow, water feed rate, catalyst feed rate, hydrocarbon feed rate, solvent feed rate, and a combination thereof, for conducting the phase-related adjustments.

64. A method as defined in claim 62, further comprising a step of correlating phase diagram data with variables selected from a group consisting of temperature in the reaction zone, pressure in the reaction zone, rate of gaseous oxidant flow, water feed rate, catalyst feed rate, hydrocarbon feed rate, solvent feed rate, and a combination thereof, for conducting the phase-related adjustments.

65. A method of controlling in a reaction zone the oxidation of a hydrocarbon to form an acid in the presence of a catalyst, a solvent, an optional promoter, and oxidation products including water, the hydrocarbon, the catalyst, the solvent, and at least part of the oxidation products including water forming at least partially a liquid mixture, the method comprising the steps of:

(a) bringing in contact the liquid mixture with a gaseous oxidant in the reaction zone at a first temperature, the first temperature being adequately high for the oxidation to proceed;

(b) conducting at least one step selected from a group consisting of (b1) taking samples of the liquid mixture during the course of the oxidation and determining phase relationships thereof;
(b2) at least periodically monitoring the phase relationships of the liquid mixture during the course of the oxidation;
(b3) at least periodically determining the presence or absence of a second liquid phase qualitatively or quantitatively;
(b4) at least periodically determining the presence or absence of more than one liquid phase; and (c) making phase-related adjustments to the liquid mixture the phase-related adjustments being at least partially based on phase formation relationships when said liquid mixture is at a second temperature.

66. A method as defined in claim 65, wherein the first and the second temperatures are substantially the same.

67. A method as defined in claim 66, wherein the phase related adjustments to the liquid mixture arc directed toward formation and maintenance of a single liquid phase at the first temperature.

68. A method as defined in claim 67, wherein the phase related adjustments to the liquid mixture are conducted by controlling in the reaction zone a variable selected from a group consisting of temperature in the reaction zone, pressure in the reaction zone, rate of gaseous oxidant flow, water feed rate, catalyst feed rate, hydrocarbon feed rate, solvent feed rate, and a combination thereof.

69. A method as defined in claim 68, wherein the hydrocarbon comprises cyclohexane, the solvent comprises acetic acid, the catalyst comprises cobalt ions, and the oxidation products comprise adipic acid and water.

70. A method as defined in claim 69, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively.

71. A method as defined in claim 70, further comprising a step of spinning the polymer into fibers.

* * * * *